United States Patent
Patil et al.

(10) Patent No.: US 12,429,543 B2
(45) Date of Patent: Sep. 30, 2025

(54) SIMULTANEOUS MULTI-SLAB THERMOMETRY DURING MR-GUIDED THERMAL THERAPY

(71) Applicants: Siemens Healthineers AG, Forchheim (DE); University of Utah Research Foundation, Salt Lake City, UT (US)

(72) Inventors: Sunil Goraksha Patil, Ellicott City, MD (US); Henrik Odeen, Salt Lake City, UT (US); Himanshu Bhat, Newton, MA (US); John Roberts, Salt Lake City, UT (US); Dennis L. Parker, Centerville, UT (US); Bradley Drake Bolster, Jr., Sandy, UT (US)

(73) Assignees: Siemens Healthineers AG, Forchheim (DE); University of Utah Research Foundation, Salt Lake City, UT (US)

( * ) Notice: Subject to any disclaimer, the term of this patent is extended or adjusted under 35 U.S.C. 154(b) by 437 days.

(21) Appl. No.: 16/390,078

(22) Filed: Apr. 22, 2019

(65) Prior Publication Data

US 2020/0333413 A1    Oct. 22, 2020

(51) Int. Cl.
*G01R 33/483* (2006.01)
*A61B 5/00* (2006.01)
(Continued)

(52) U.S. Cl.
CPC ........ *G01R 33/4835* (2013.01); *A61B 5/0042* (2013.01); *A61B 5/01* (2013.01);
(Continued)

(58) Field of Classification Search
CPC ............ G01R 33/4835; G01R 33/4808; G01R 33/5616; G01R 33/543; G01R 33/4818;
(Continued)

(56) References Cited

U.S. PATENT DOCUMENTS 9,116,219 B1 *   8/2015  Posse ................ G01R 33/4806
9,271,794 B2 *   3/2016  Tyc ...................... A61N 5/0601
(Continued)

FOREIGN PATENT DOCUMENTS

JP        4509256 B2 *  7/2010  ............. A61B 6/032
WO    WO-2004104611 A2 * 12/2004  ........... G01R 33/287
WO    WO-2013124299 A1 *  8/2013  ......... G01R 33/4804

OTHER PUBLICATIONS

Ozhinsky E, Salgaonkar VA, Diederich CJ, Rieke V; "MR Thermometry-Guided Ultrasound Hyperthermia of User-Defined Regions Using the ExAblate Prostate Ablation Array"; Aug. 13, 2018 (Year: 2018).*

(Continued)

*Primary Examiner* — John D Li

(57) ABSTRACT

A method for performing magnetic resonance-guided thermal therapy includes selecting a first set of sampling characteristics for acquiring a first set of slabs covering a first anatomical region of interest. Additionally, a second set of sampling characteristics is selected for acquiring a second set of slabs covering a second anatomical region of interest. This second set of sampling characteristics is distinct from the first set of sampling characteristics. An interleaved acquisition of the first set of slabs and the second set of slabs may then be performed using the first set of sampling characteristics and the second set of sampling characteristics.

15 Claims, 6 Drawing Sheets

(51) Int. Cl.
  *A61B 5/01* (2006.01)
  *A61B 5/055* (2006.01)
  *G01R 33/48* (2006.01)
  *G01R 33/54* (2006.01)
  *G01R 33/561* (2006.01)
(52) U.S. Cl.
  CPC ............ *A61B 5/055* (2013.01); *A61B 5/7275* (2013.01); *G01R 33/4808* (2013.01); *G01R 33/543* (2013.01); *G01R 33/5616* (2013.01)
(58) Field of Classification Search
  CPC ........................ G01R 33/4814; G01R 33/4804; A61B 5/055; A61B 5/01; A61B 5/7275; A61B 5/0042; A61B 5/015
  See application file for complete search history.

(56) References Cited

U.S. PATENT DOCUMENTS

| | | | | |
|---|---|---|---|---|
| 9,977,104 | B2* | 5/2018 | Vahala | G01R 33/543 |
| 2006/0206105 | A1* | 9/2006 | Chopra | A61B 5/055 |
| | | | | 607/96 |
| 2009/0147074 | A1* | 6/2009 | Getty | H04N 13/275 |
| | | | | 348/51 |
| 2014/0077809 | A1* | 3/2014 | Schmidt | G01R 33/5619 |
| | | | | 324/309 |
| 2014/0184221 | A1* | 7/2014 | Son | G01R 33/5619 |
| | | | | 324/309 |
| 2014/0194728 | A1* | 7/2014 | Vahala | G01R 33/285 |
| | | | | 600/411 |
| 2014/0270453 | A1* | 9/2014 | Guo | G01R 33/50 |
| | | | | 382/131 |
| 2015/0190659 | A1* | 7/2015 | Kohler | A61N 7/02 |
| | | | | 600/411 |
| 2016/0047874 | A1* | 2/2016 | Grodzki | G01R 33/5635 |
| | | | | 324/309 |
| 2016/0109539 | A1* | 4/2016 | Mardor | A61B 5/4848 |
| | | | | 600/420 |
| 2016/0157746 | A1* | 6/2016 | Ellingson | G01R 33/56341 |
| | | | | 600/420 |
| 2016/0273970 | A1* | 9/2016 | Alon | G01K 3/08 |
| 2017/0082715 | A1* | 3/2017 | Choi | G01R 33/561 |
| 2017/0203131 | A1* | 7/2017 | Carol | A61B 8/4444 |

OTHER PUBLICATIONS

Odéen et al. "Sampling strategies for subsampled segmented EPI PRF thermometry in MR guided high intensity focused ultrasound." Med Phys. Sep. 2014; 41(9): 092301.*
Jagannathan et al. "High intensity focused ultrasound surgery (HIFU) of the brain: A historical perspective, with modern applications." Neurosurgery. Feb. 2009; 64(2): 201-211.*
A method to extract image noise level from patient images in CT ; Annelise Malkus; published Apr. 25, 2017 (Year: 2017).*
Setsompop, Kawin et al. "Blipped-Controlled Aliasing in Parallel Imaging for Simultaneous Multislice Echo Planar Imaging With Reduced g-Factor Penalty" Magnetic Resonance in Medicine; vol. 67; No. 5; pp. 1210-1224, 2012.

* cited by examiner

SIMULTANEOUS MULTI-SLAB THERMOMETRY DURING MR-GUIDED THERMAL THERAPY

TECHNOLOGY FIELD

The present invention relates generally to methods, systems, and apparatuses for the use of simultaneous multi-slab thermometry techniques during MR-guided thermal therapy. The disclosed methods, systems, and apparatuses may be applied to various thermal therapy clinical applications including, for example, Laser Induced Thermotherapy (LITT), High Intensity Focused Ultrasound (HIFU), Radiofrequency Ablation (RFA), and cryo-ablation

BACKGROUND

Magnetic resonance (MR) thermometry refers to tracking temperature changes in tissue of a patient using magnetic resonance image (MRI). An important application for MR thermometry is for monitoring temperature changes due to thermal therapy. Thermal therapy refers to the ablation of tissue of a patient using hot or cold temperatures. Thermal therapy can be advantageous to surgical, chemotherapy, and radiotherapy applications.

In thermal therapy, the induced temperature rise introduces a change in the shielding of the hydrogen protons due to bending, stretching and breaking of hydrogen bonds between water molecules. This reduces the fraction of the $B_0$ magnetic field experienced by the water protons, resulting in a decrease in the resonance frequency. The well-known proton resonance frequency shift (PRFS) based MR thermometry method captures this temperature change by subtracting the phase images before the thermal therapy (baseline) from the ones with temperature rise (i.e., during thermal therapy). Temperature differences ($\Delta T$) are calculated by:

$$\Delta T = \frac{\phi_{therm} - \phi_{base}}{\alpha \gamma B_0 TE} = \frac{\Delta \phi}{\alpha \gamma B_0 TE}$$

where $\gamma$ is the gyromagnetic ratio (in Hz/Tesla), $B_0$ is the static magnetic field strength (in Tesla), TE is echo time (in ms), $\emptyset_{therm}$ and $\emptyset_{base}$ are phase images (in radians) at baseline and thermal therapy, respectively. $\alpha$ is the temperature coefficient which is typically 0.01 ppm/° C. for the temperature range of interest.

MR thermometry typically utilizes a one or a few 2D slices or a thin 3D slab placed around the region of heating. However, inadvertent heating outside the intended target zone may occur. This is especially true for high intensity focused ultrasound applications where near- and far-field heating, especially around bones, is commonly seen. Increasing the number of 2D slices or the thickness of a 3D slab to monitor a larger field of view leads to decreased temporal resolution (i.e., longer scan times). Hence, efficient methods to simultaneously monitor $\Delta T$ in two or more zones, covering both the target region and the near- and/or far field, are highly desirable from a safety perspective.

SUMMARY

Embodiments of the present invention address and overcome one or more of the above shortcomings and drawbacks, by providing methods, systems, and apparatuses related to multi-slab acquisition techniques for MR-guided thermal therapy applications.

According to some embodiments, a method includes selecting a first set of sampling characteristics for acquiring a first set of slabs covering a first anatomical region of interest. Additionally, a second set of sampling characteristics is selected for acquiring a second set of slabs covering a second anatomical region of interest. This second set of sampling characteristics is distinct from the first set of sampling characteristics. An interleaved acquisition of the first set of slabs and the second set of slabs may then be performed using the first set of sampling characteristics and the second set of sampling characteristics. Alternatively, a simultaneous multi-slab acquisition of the first set of slabs and the second set of slabs may be performed using the first set of sampling characteristics and the second set of sampling characteristics. In this case, the first and second set of slabs are simultaneously excited and sampled during the simultaneous multi-slab acquisition.

In other embodiments of the present invention, a system comprises a central control computer unit (i) selecting a first set of sampling characteristics for acquiring a first set of slabs covering a first anatomical region of interest and (ii) selecting a second set of sampling characteristics for acquiring a second set of slabs covering a second anatomical region of interest. Again, this second set of sampling characteristics is distinct from the first set of sampling characteristics. The system may then include an imaging device that performs an interleaved acquisition of the first set of slabs and the second set of slabs using the first set of sampling characteristics and the second set of sampling characteristics. Alternatively (or additionally), the imaging device may perform a simultaneous multi-slab acquisition of the first set of slabs and the second set of slabs using the first set of sampling characteristics and the second set of sampling characteristics.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses for performing MR-guided thermal therapy using a simultaneous multi-slab approach. More specifically, instead of using a large contiguous 3D slab to cover both the treatment area and peripheral areas of interest, a plurality of thinner slabs are positioned such that the sensitive peripheral at-risk areas are monitored, interleaved or simultaneously with the focal area, requiring reduced encoding to monitor temperature at sufficient temporal and spatial resolution in all regions of interest.

The term "slab" refers to an excited 3D volume. Slabs are often referred to as either "thin" or "thick." The exact definition of the terms "thin" and "thick" can vary depending on factors such as the clinical study being performed and the anatomy being imaged. One example definition is that slabs less than 5 mm in thickness are considered "thin," while those above 5 mm are considered "thick."

The term "multi-slab imaging" refers to the acquisition of multiple slabs (i.e., 3D volumes) during a single scan. One conventional example of multi-slab imaging is the Time of Flight (TOF) technique where the blood inflow of non-saturated spins is used to depict blood vessels. As a result of being non-saturated, these spins give more signal than surrounding stationary spins. With this technique, data in the area of interest is typically acquired using a thin slab so as to optimize the vessel contrast.

Figure 1:
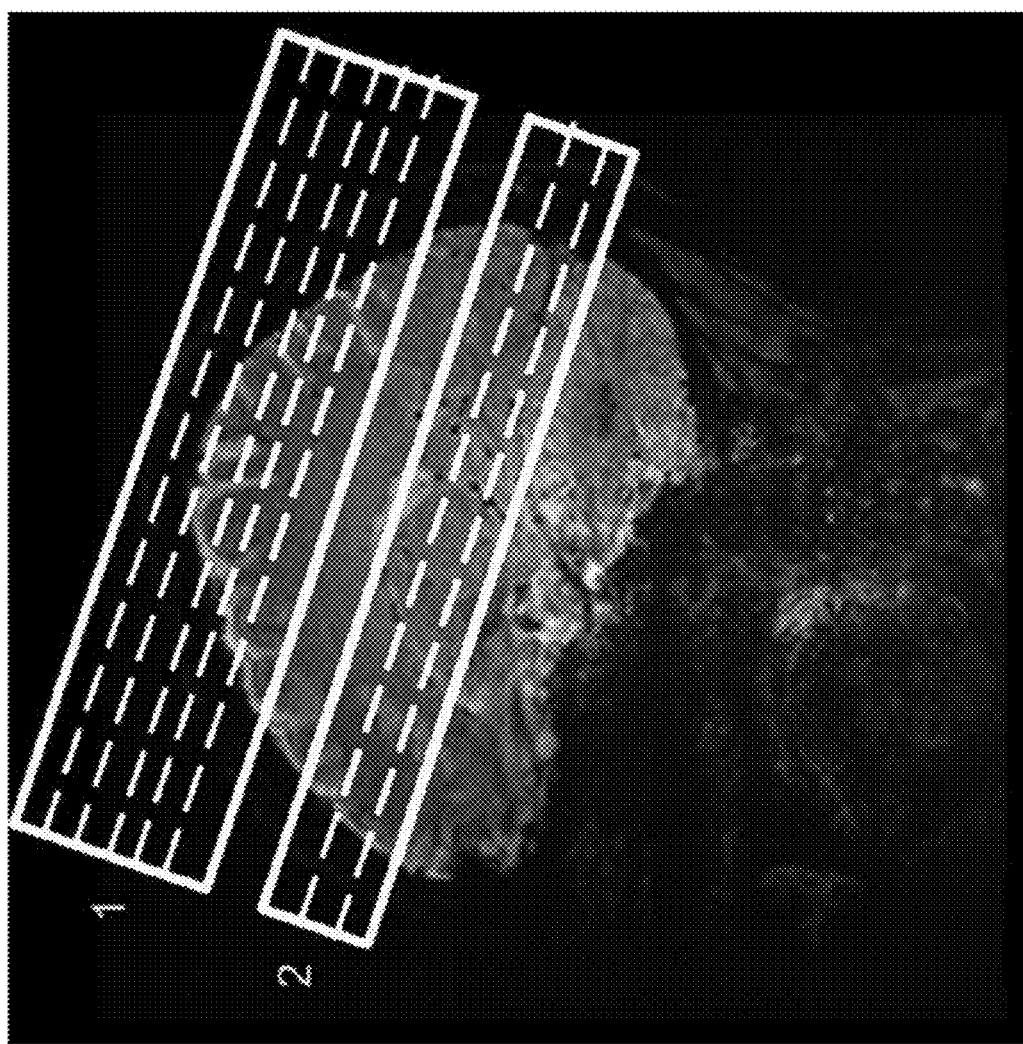
FIG. 1 provides a conceptual overview of how simultaneous multi-slab thermometry techniques can be performed during MR-guided thermal therapy, according to some embodiments.

FIG. 1 provides a conceptual overview of how simultaneous multi-slab thermometry techniques can be performed during MR-guided thermal therapy, according to some embodiments. This example depicts a transcranial, high intensity focused ultrasound (HIFU) treatment. During such treatments, the patient's head is surrounded by a transducer which non-invasively is focusing ultrasound to a small focal spot within the brain. Due to the high acoustic absorption of bone, this setup may lead to inadvertent heating of the skull bone over the length of a treatment.

In the example of FIG. 1, two different sets of slabs are used for simultaneous temperature change monitoring of the cortex (non-intended-heating zone) and focal spot treatment zone (intended heating zone). Each slab has independent sampling characteristics that can be independently adjusted. A thick slab is positioned to interrogate the cortex at lower spatial resolution, while a second, thinner, higher resolution slab is positioned over the focal area to measure the therapy with a higher update rate. Because the peripheral zones would be expected to heat at a slower rate, the thicker slab could be updated less often than the thinner slab position over the therapy focus.

The term "sampling characteristics" refers to any parameters associated with acquisition of a slab. For example, in some embodiments, the sampling characteristics specify the thickness of the slabs used for the acquisition. This thickness value may be specified, for example, as a metric measurement (e.g., centimeters, millimeters, etc.) or using any other indicator generally known in the art. In some embodiments, spatial and/or temporal resolution parameters may be specified as part of the sampling characteristics. Spatial resolution may be specified, for example, in millimeters, while temporal resolution can be specified in units such as milliseconds. In other embodiments, contrast resolution (e.g., low, moderate, high, etc.) or a different type of contrast parameter may be specified as an acquisition characteristic.

Figure 2:
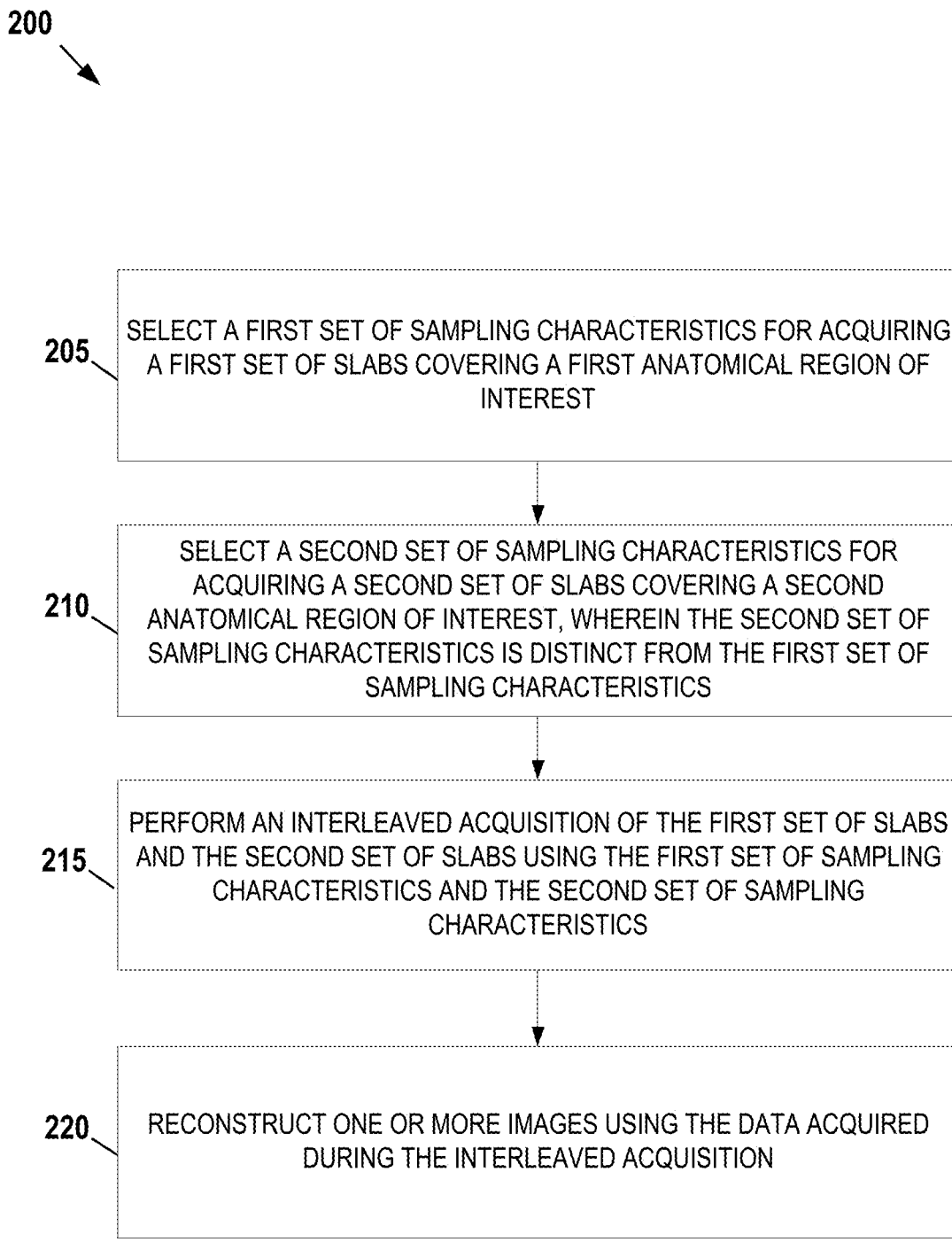
FIG. 2 provides a flowchart illustrating a method for performing an interleaved, simultaneous multi-slab acquisition according to some embodiments.

FIG. 2 provides a flowchart illustrating a method 200 for performing an interleaved, simultaneous multi-slab acquisition according to some embodiments. In this example, a plurality of slabs is acquired interleaved with one another. One benefit of the interleaved acquisition is that each slab can have different sampling characteristics such as thickness, spatial resolution temporal resolution, field of view, and/or contrasts. Further, the interleaved acquisition technique facilitates the application of multiple parallel imaging techniques independently in the different slabs. Alternatively (or additionally), partial Fourier approaches may be used to vary how much time is spent sampling in each slab.

Starting at steps 205 and 210, input parameters are selected for performing the acquisition. This selection may be performed manually, for example, as a result of user input or automatically as part of a workflow for a particular thermal therapy application. In this example, application calls for dividing the anatomical area of interest into two sections (e.g., cortex and focal area). It should be understood, this example can be scaled to greater numbers of sections using techniques which are similar to those presented in FIG. 2. The selection performed at steps 205 and 210 is based on the anatomical area of interest. Specifically, at step 205, a first set of sampling characteristics are selected for acquiring a first set of slabs covering a first anatomical region of interest. Similarly, at step 210, a second set of sampling characteristics are selected for acquiring a second set of slabs covering a second anatomical region of interest. This second set of sampling characteristics is distinct from the first set of sampling characteristics.

Figure 5A:
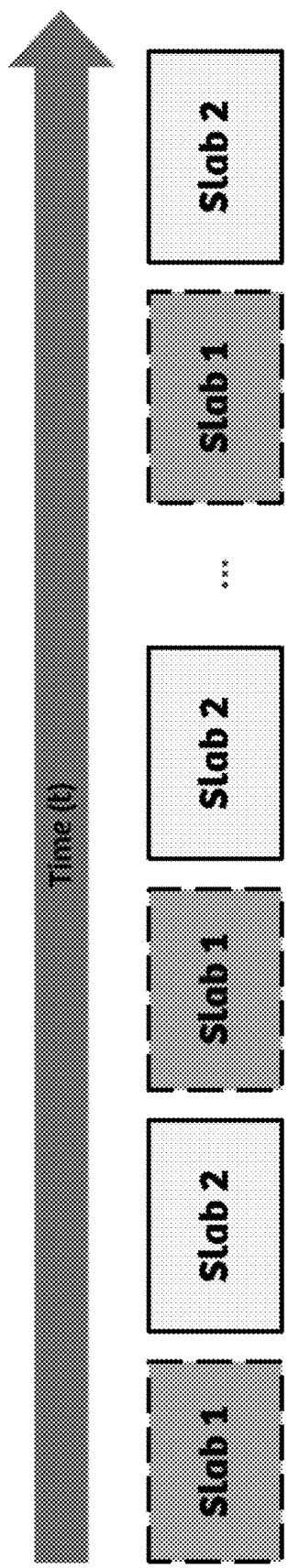
FIG. 5A shows one example of an interleaving scheme used in some embodiments of the present invention.
Figure 5B:
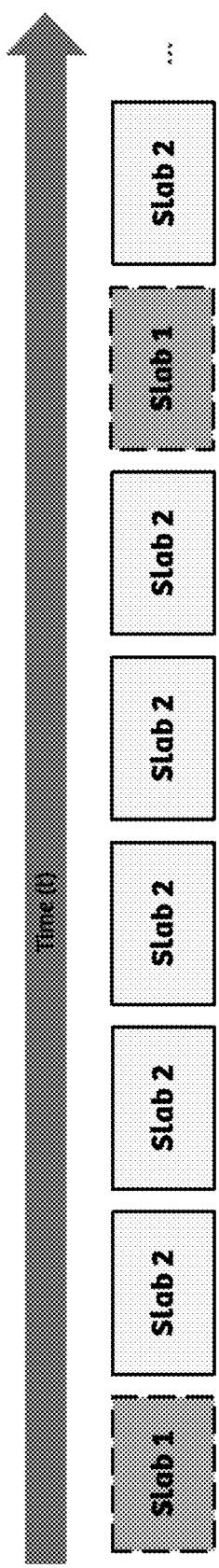
FIG. 5B shows a second example of an interleaving scheme used in some embodiments of the present invention.

Next, at step 215, the MRI scanner performs an interleaved acquisition of the first and second sets of slabs using the first set and second set of sampling characteristics. Various interleaving techniques may be used to acquire the k-space data corresponding to each set of slabs. For example, the frequency of interleaving could be set through a user input. In one embodiment, first set of slabs is alternated with second set of slabs. i.e., the second set of slabs is acquired after every first set of slabs, as shown in FIG. 5A. In another embodiment, (shown in FIG. 5B), application of first set of slabs is interleaved with five second set of slabs, i.e., the first set of slabs is acquired after every five second set of slabs. Returning to FIG. 2, at step 220, one or more images are reconstructed using the data acquired during the interleaved acquisition. Techniques for performing such reconstruction are generally known in the art and, thus, these techniques are not described herein in full detail.

Figure 3:
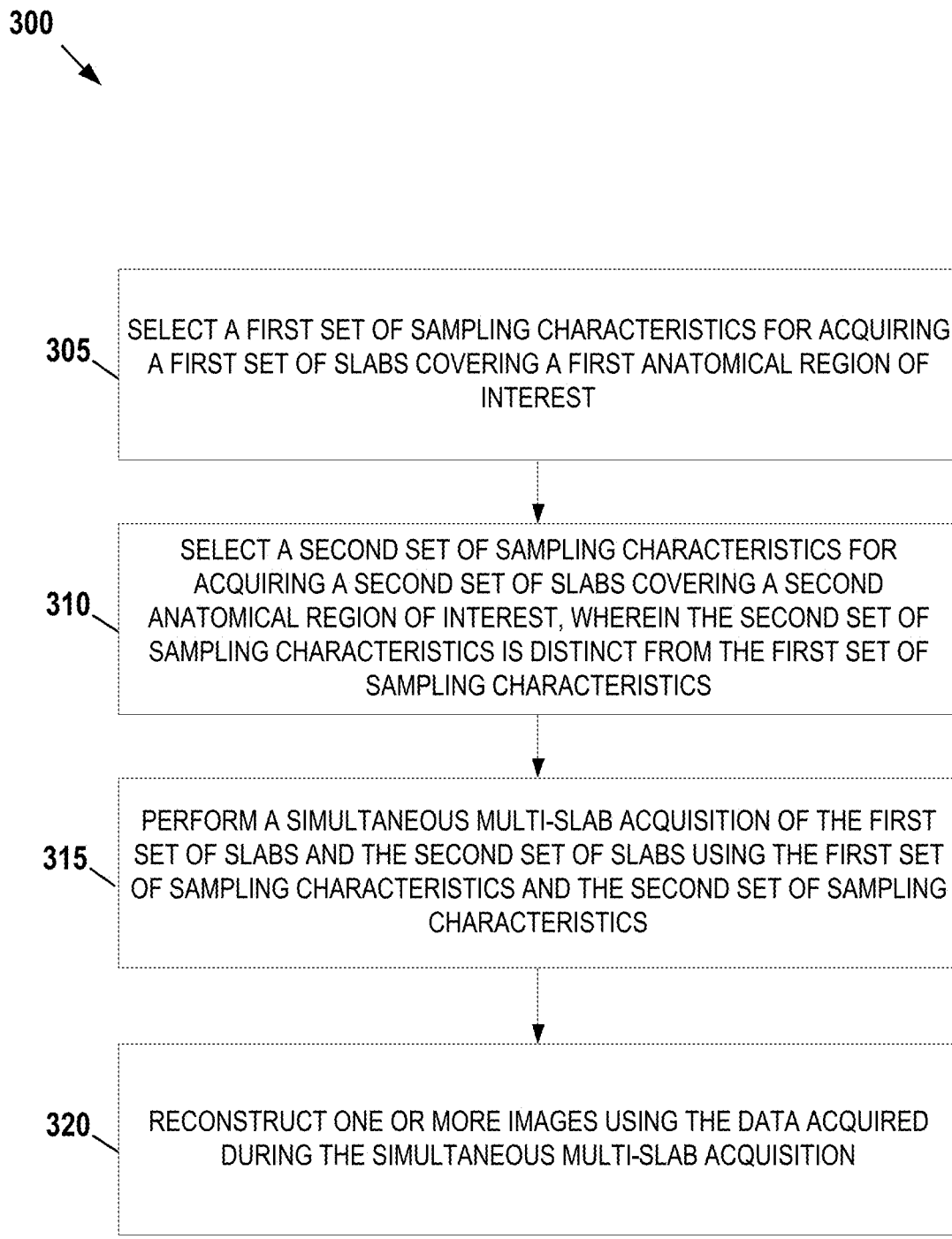
FIG. 3 shows an alternative method where the slabs are simultaneously acquired.

FIG. 3 shows an alternative method 300 where the slabs are simultaneously acquired. A technique called simultaneous multi-slice (SMS) has been published for accelerating MR data acquisition, reducing the time the patient spends in the MR scanner. Details of the SMS technique, particularly as applicable to Echo Planar Imaging (EPI)-based acquisitions, can be found in the article "Setsompop et al. Blipped-Controlled Aliasing in Parallel Imaging for Simultaneous Multi-Slice Echo Planar Imaging with Reduced g-factor Penalty", MRM, Vol. 67(5), pp. 1210-1224 (2012). In general, the SMS technique involves the simultaneous excitation and sampling of a number of 2D slices within the volume that is to be imaged. The individual slices can be separated in post-processing, utilizing parallel imaging approaches including, without limitation, the slice GRAPPA or the CAIPI techniques.

In FIG. 3, steps 305 and 310 are similar to steps 205 and 210 in FIG. 2. That is, the sampling characteristics of a first set of slabs are selected at step 305, while the sampling characteristics of a second set of slabs are selected at step 310. At step 315, the first set of slabs and second set of slabs are simultaneously acquired by using a technique that adapts SMS procedure to Simultaneous Multi-Slab (SMSlab) imaging in which two or more slabs are excited and acquired simultaneously either as a GRE or segmented/single-shot EPI acquisitions. This enables simultaneous monitoring of AT in two or more 3D slabs. Like the interleaved case described in FIG. 2, using a slab acceleration factor of 2, one slab can be positioned, for example, to cover the intended target zone while another covers the area of the skull at risk. These simultaneously excited slabs can have the same slab thickness as is typical for SMS or the technique could be extended to allow for slabs of varying thicknesses. Temporal and spatial resolution in these SMSlab cases may be handled similarly. Finally, at step 320, one or more images are reconstructed using the data acquired during the SMSlab acquisition. As compared to interleaved strategy, such an acquisition scheme would lead to simultaneous monitoring of ΔT while keeping the same temporal resolution overall.

Figure 4:
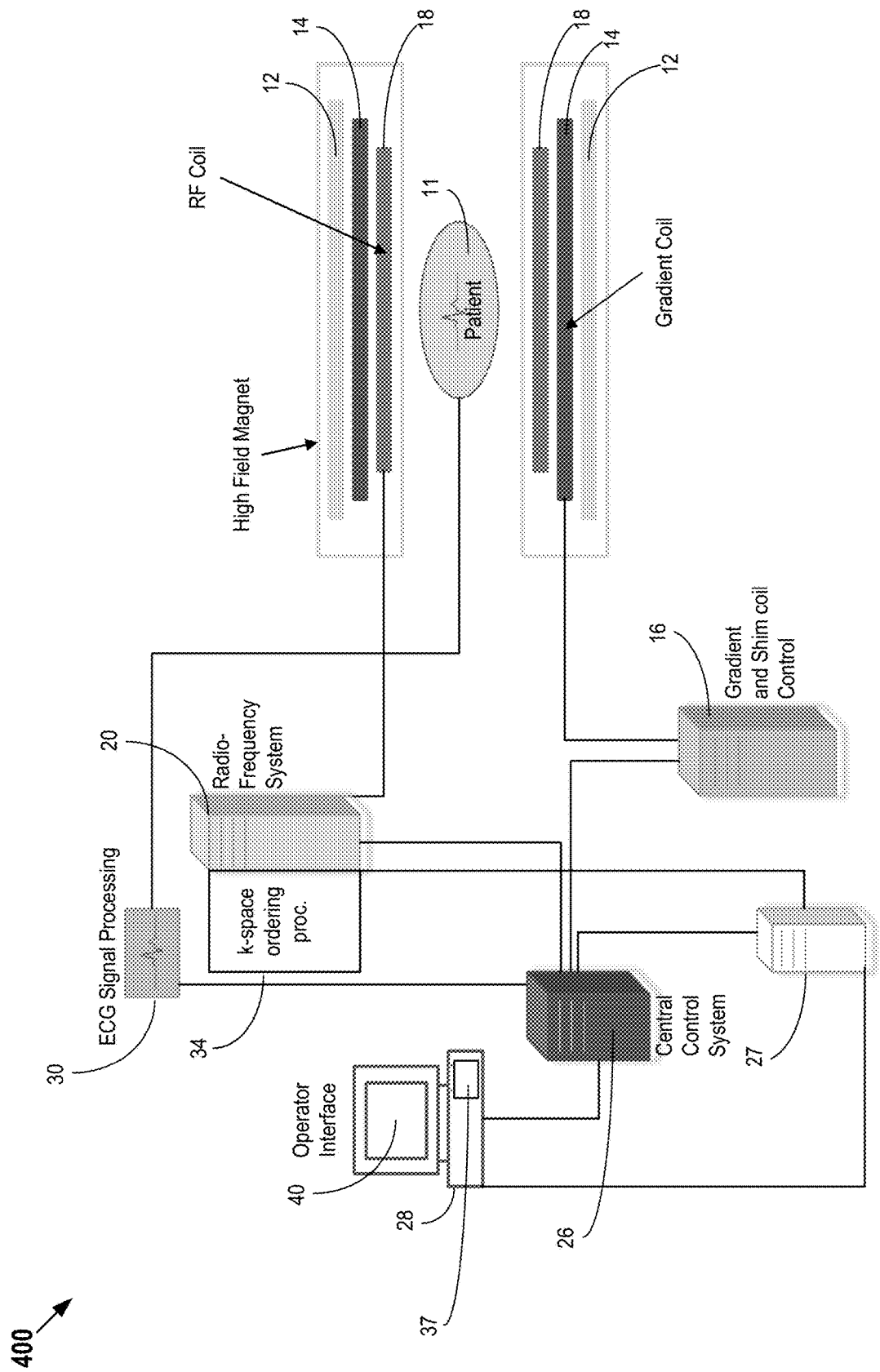
FIG. 4 shows a system for ordering acquisition of frequency domain components representing magnetic resonance (MR) image data for storage in a k-space storage array, as used by some embodiments of the present invention.

FIG. 4 shows a system 400 for ordering acquisition of frequency domain components representing MR image data for storage in a k-space storage array, as used by some embodiments of the present invention. In system 400, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field and a readout gradient magnetic field that are applied to patient 11.

Further RF (radio frequency) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11. For example, as described in greater detail below, in some embodiments, the central control unit 26 directs the various components of the system 400 to acquire radial k-space data using a bSSFP sequence with an interleaved-angle asymmetric radial sampling scheme.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor unit 34 to provide an MR dataset to an image data processor for processing into an image. In some embodiments, the image data processor is located in central control unit 26. However, in other embodiments such as the one depicted in FIG. 4, the image data processor is located in a separate unit 27. ECG synchronization signal generator 30 provides ECG signals used for pulse sequence and imaging synchronization. A two or three dimensional k-space storage array of individual data elements in k-space component processor unit 34 stores corresponding individual frequency components comprising an MR dataset. The k-space array of individual data elements has a designated center and individual data elements individually have a radius to the designated center.

A magnetic field generator (comprising coils 12, 14 and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components is sequentially acquired during acquisition of an MR dataset representing an MR image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components is substantially minimized.

Central control unit 26 uses information stored in an internal database to process the detected MR signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on the display 40 of the operator interface. Computer 28 of the operator interface includes a graphical user interface (GUI) enabling user interaction with central control unit 26 and enables user modification of magnetic resonance imaging signals in substantially real time. Display processor 37 processes the magnetic resonance signals to provide image representative data for display on display 40, for example.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

The term "computer readable medium" as used herein refers to any medium that participates in providing instructions to the processor for execution. A computer readable medium may take many forms including, but not limited to, non-volatile media, volatile media, and transmission media.

Non-limiting examples of non-volatile media include optical disks, solid state drives, magnetic disks, and magneto-optical disks, such as hard disk or removable media drive. One non-limiting examples of volatile media is dynamic memory. Non-limiting examples of transmission media include coaxial cables, copper wire, and fiber optics, including the wires that make up one or more buses. Transmission media may also take the form of acoustic or light waves, such as those generated during radio wave and infrared data communications.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f), unless the element is expressly recited using the phrase "means for."

We claim:

1. A method comprising:
    performing thermal therapy on an intended area located within a first anatomical region of interest, while limiting heating to an unintended area of a second anatomical region of interest; and
    performing an interleaved acquisition, during the thermal therapy, of a first set of slabs in a first 3D volume that covers the first anatomical region of interest using a first set of sampling characteristics and a second set of slabs in a second 3D volume that covers the second anatomical region of interest using a second set of sampling characteristics, the first set of sampling characteristics including a first thickness parameter and the second set of sampling characteristics including a second thickness parameter,
    wherein the first and second 3D volumes do not overlap; and
    wherein the second thickness parameter for the second set of slabs covering the unintended area is greater than the first thickness parameter for the first set of slabs.

2. The method of claim 1, wherein the first thickness parameter and the second thickness parameter each comprise a slab volume thickness parameter.

3. The method of claim 1, wherein the first set of sampling characteristics and the second set of sampling characteristics each comprise different spatial resolution parameters.

4. The method of claim 1, wherein the first set of sampling characteristics and the second set of sampling characteristics each comprise different temporal resolution parameters.

5. The method of claim 1, wherein the first set of sampling characteristics and the second set of sampling characteristics each comprise different contrast parameters.

6. The method of claim 1, wherein
    the first set of sampling characteristics specify a first spatial resolution parameter, and
    the second set of sampling characteristics specify a second spatial resolution parameter corresponding to a lower spatial resolution value in comparison to the first spatial resolution parameter.

7. The method of claim 6, wherein the first anatomical region of interest is a focal area of a subject's brain and the second anatomical region of interest is a cortex of the subject's brain.

8. The method of claim 1, wherein the interleaved acquisition is performed using as a segmented/single-shot echo planar imaging (EPI) acquisition.

9. The method of claim 1, wherein the interleaved acquisition is performed using as a gradient echo (GE) acquisition.

10. The method of claim 1, wherein the first set of slabs are acquired after five of the second set of slabs.

11. The method of claim 1, wherein the first set of sampling characteristics are adjustable independently of the second set of sampling characteristics.

12. The method of claim 1, wherein the first set of slabs have a thickness of less than 5 mm.

13. A system comprising:
    an imaging device configured to perform an interleaved acquisition of (i) a first set of excited 3D slabs using a first set of sampling characteristics, the first set of excited 3D slabs covering a first anatomical region of interest, and the first set of sampling characteristics including a first thickness parameter, and (ii) a second set of excited 3D slabs using a second set of sampling characteristics, the second set of excited 3D slabs covering a second anatomical region of interest, wherein the first and second sets of excited 3D slabs do not overlap, the second set of sampling characteristics is distinct from the first set of sampling characteristics, and the second set of sampling characteristics include a second thickness parameter;
    wherein the second thickness parameter for the second set of slabs covering an unintended area, at which heating is limited, is greater than the first thickness parameter for the first set of slabs.

14. The system of claim 13, further comprising:
a therapy device configured to perform thermal therapy on an intended area located within the first anatomical region of interest, while limiting heating to the unintended area.

15. The system of claim 13, further comprising:
a central controller configured to select the first set of sampling characteristics and the second set of sampling characteristics; and
wherein the first set of sampling characteristics is different from the second set of sampling characteristics.

* * * * *